United States Patent
Cerutti

(10) Patent No.: US 7,498,823 B2
(45) Date of Patent: Mar. 3, 2009

(54) PHYSICAL QUANTITY, PARTICULARLY HUMIDITY DETECTION DEVICE, AND RELATED DETECTING METHOD

(75) Inventor: Walter Cerutti, Arnad (IT)

(73) Assignee: Telecom Italia S.p.A., Milan (IT)

( * ) Notice: Subject to any disclaimer, the term of this patent is extended or adjusted under 35 U.S.C. 154(b) by 140 days.

(21) Appl. No.: 11/630,239

(22) PCT Filed: Jun. 14, 2005

(86) PCT No.: PCT/EP2005/006349

§ 371 (c)(1),
(2), (4) Date: Dec. 21, 2006

(87) PCT Pub. No.: WO2005/124327

PCT Pub. Date: Dec. 29, 2005

(65) Prior Publication Data

US 2008/0028853 A1      Feb. 7, 2008

(30) Foreign Application Priority Data

Jun. 21, 2004    (IT) .......................... TO2004A0411

(51) Int. Cl.
*G01R 27/08* (2006.01)
(52) U.S. Cl. .................. 324/694; 73/335.02; 73/204.15; 73/23.2; 219/497; 324/713; 324/662
(58) Field of Classification Search .................. 324/694
See application file for complete search history.

(56) References Cited

U.S. PATENT DOCUMENTS

| | | | |
|---|---|---|---|
| 3,582,728 A | 6/1971 | Thoma | |
| 3,675,484 A * | 7/1972 | Pederson | 331/66 |
| 3,731,535 A * | 5/1973 | Wendt, Jr. | 374/114 |
| 3,775,843 A * | 12/1973 | Wendt, Jr. | 29/612 |
| 4,404,462 A * | 9/1983 | Murray | 219/497 |
| 4,442,422 A | 4/1984 | Murata et al. | |
| 4,572,900 A | 2/1986 | Wohltjen | |
| 4,642,601 A | 2/1987 | Sugawara et al. | |
| 4,717,811 A * | 1/1988 | Fujii | 219/497 |

(Continued)

FOREIGN PATENT DOCUMENTS

| CN | 2543063 Y | 4/2003 |
|---|---|---|
| EP | 0 687 903 | 12/1995 |
| EP | 0 816 805 | 1/1998 |
| EP | 0 844 477 | 5/1998 |

(Continued)

OTHER PUBLICATIONS

International Search Report from PCT/EP2005/006349, mailed Oct. 12, 2005.

*Primary Examiner*—Timothy J Dole
*Assistant Examiner*—Benjamin M Baldridge
(74) *Attorney, Agent, or Firm*—Venable LLP; Robert Kinberg; Steven J. Schwarz

(57) ABSTRACT

A pair of identical humidity sensors (S1) and (S2) are in the same environment, so that they identically react to humidity effects; a sensing circuit includes an operational amplifier (10), its input (15) receiving from the first sensor (Si) a signal changing with humidity according to a logarithmic law, while the second sensor (S2), inserted in the amplifier feedback, reacts to humidity changes in the same way as the first sensor (Si) and consistently modifies the gain. The output signal ($V_o$) is compensated, and has a substantially linear progression with humidity.

20 Claims, 7 Drawing Sheets

U.S. PATENT DOCUMENTS

| | | |
|---|---|---|
| 4,793,175 A | 12/1988 | Fedter et al. |
| 4,868,390 A * | 9/1989 | Keller et al. ............. 250/338.3 |
| 5,040,090 A | 8/1991 | Birkle et al. |
| 5,341,287 A * | 8/1994 | Cordier et al. ................ 700/28 |
| 5,394,746 A * | 3/1995 | Williams ................ 73/204.15 |
| 5,406,137 A | 4/1995 | Scheler et al. |
| 5,414,441 A * | 5/1995 | Memarzadeh et al. ......... 345/87 |
| 5,546,802 A | 8/1996 | Yoshimura et al. |
| 5,652,382 A * | 7/1997 | Nakagawa et al. ....... 73/355.02 |
| 6,189,385 B1 * | 2/2001 | Horiuchi et al. ............... 73/664 |
| 6,220,076 B1 * | 4/2001 | Layzell et al. ............... 73/23.2 |
| 6,229,318 B1 | 5/2001 | Suda |
| 7,012,466 B2 * | 3/2006 | Cerisola ..................... 330/260 |
| 7,378,856 B2 * | 5/2008 | Peine et al. ................. 324/662 |
| 2002/0087281 A1 * | 7/2002 | More ........................ 702/107 |
| 2002/0190733 A1 * | 12/2002 | Kinoshita et al. ........... 324/713 |

FOREIGN PATENT DOCUMENTS

| | | |
|---|---|---|
| EP | 0 884 592 | 12/1998 |
| EP | 0 942 281 | 9/1999 |
| JP | 60177253 A * | 9/1985 |
| JP | 06109677 A * | 4/1994 |

* cited by examiner

PHYSICAL QUANTITY, PARTICULARLY HUMIDITY DETECTION DEVICE, AND RELATED DETECTING METHOD

TECHNOLOGICAL FIELD OF THE INVENTION

The present invention relates to a physical quantity, particularly humidity detection device, and to the related method of detection, and more in particular it relates to a sensing circuit suitable to detect and process the data provided by a physical quantity, particularly humidity sensor, detected in open environments, or in inaccessible places.

BRIEF DESCRIPTION OF THE STATE OF THE ART

Physical quantity, particularly humidity detection devices are well known in the current art, which are based on different detection techniques and different constructions of the sensors used; in particular, among the constructions used in the art in order to make humidity sensors, the most recurrent one consists of using a chemically inert support, on which generally a double array of conductors are deposited, interlaced with and insulated from one another, covered by a layer of a material sensitive to humidity, having electric characteristics, such as resistivity or dielectric constant, depending on the humidity in the environment where the sensor is plunged.

Humidity sensors known in the art use, as a material sensitive to humidity, electrically conductive materials, which have a resistivity changing with humidity, as described in U.S. Pat. No. 6,229,318, or dielectric materials whose dielectric constant changes with humidity, as described in U.S. Pat. No. 3,582,728.

In U.S. Pat. No. 4,642,601 and U.S. Pat. No. 4,793,175, among materials of a resistive type, conductive hydrophilic polymers, sintered ceramic powders, resins, or properly treated metal salt-based compounds are mentioned.

However, the applicant has observed that the resistive sensors described in the above mentioned documents have a logarithmic type of response, difficult to be represented and very inexact below 20% of relative humidity (RH), which requires sophisticate electronic apparatus for the subsequent processing. On the other hand, resistive type sensors offer a very good interchangeability and require low cost manufacturing.

Materials of a capacitive type, comprised of ceramic compounds or dielectric polymers, such as for example cellulose-acetate butyrate (CAB) or polymethyl methacrylate, are described in U.S. Pat. No. 3,582,728 and U.S. Pat. No. 4,442,422.

The applicant has observed that the capacitive-type sensors described in the preceding documents require a very expensive processing compared with resistive sensors, but on the other hand they present a substantially linear response relative to humidity, require a simple electronic and work in a wide range of humidity.

Sensors based on resistive type materials described in the preceding documents can be supplied with direct voltage, or with unipolar pulses, while sensors using the materials of a capacitive type mentioned above must necessarily be supplied by an alternating voltage, with a waveform chosen in relation to the characteristics of the humidity sensitive material and to the type of response required from the sensor.

U.S. Pat. No. 5,040,090 mentions humidity sensors which use, as humidity sensitive materials, electrolyte polymerics compounds, made of ionic conduction resins, which present the electrolytic dissociation phenomenon in the presence of water, as for example, crossed-link copolymers of styrene sulphonate and polyvinyl chloride, copolymers of ionic or non-ionic monomers, poly-4-vinylpyridine reticulated with dibromobutane; U.S. Pat. No. 5,546,802 also mentions cross-linked conductive polymers having ethylenically unsaturated groups.

In U.S. Pat. No. 6,229,318 a humidity measuring device of a resistive type is described, made of a humidity sensor and a temperature sensor having the same temperature characteristics as the humidity sensor, but protected by a non-hygroscopic layer; in both sensors, the electrodes are deposited on a support comprised of a carbonaceous porous material, obtained by sintering and carbonizing blends of wood and paper residuals, with thermosetting resins added.

The two sensors are connected in series in a sensing circuit, and are supplied by a current Is; the voltage fall at the ends of each of the two sensors is sent to a subtractive differential amplifier, properly fed back in such a way as to generate an output equal to zero volts for null RH and a maximum output for RH equal to 100%.

The applicant observes that as the amplifier introduces only a limited compensation of the non-linearity of the humidity sensor response, this circuit does not totally solve the problem.

Another relative humidity detection device is described in U.S. Pat. No. 5,406,137; a sensing circuit uses a capacitive sensor, which capacity changes with humidity; a "one-shot" circuit generates a pulse, the duration of which is determined by the sensor capacity; this circuit is synchronized on the falling edge of each pulse generated by a multivibrator; the pulses produced by the "one-shot" circuit are integrated by an R-C net to produce a voltage proportional to the average duration of the pulses; such voltage is sent to a correction circuit, which output feeds back a multivibrator supply circuit to modify the duration and the interval of the pulses generated by the multivibrator; moreover the supply voltage of the multivibrator and the "one-shot" circuit can be manually changed with a potentiometer, in such a way as to correct the non-linearity of the sensor response to humidity changes and to maintain the calibration at an optimal value.

The applicant observes that this circuit is constructionally very complex and of not much reliable use due to the continuous manual adjustments required to maintain in time the measurement precision required.

Within the present invention the applicant has perceived the problem of creating a humidity detection device capable of providing a substantially linear relation between humidity values and the non-linear response of the humidity sensor, and with a constant precision on the whole range of measurement.

Within the present invention the applicant has perceived the problem of creating a humidity detection device capable of providing a humidity measurement independent of temperature changes in the environment wherein the sensor is placed.

The applicant has perceived that the signal of a physical quantity detection device could have been made with a linear progression and independent of temperature by means of using two sensors exposed to the same quantity, by using the signal of one of said sensors to modulate the gain of an amplifier of a signal of the other sensor.

In a first aspect, the present invention relates to a physical quantity detection device, including a sensor, sensitive to said physical quantity and exposed thereto, and an amplifier, connected to said sensor output by a first input and having a second reference input, which comprises a second sensor, sensitive to said physical quantity and exposed thereto, connected to the amplifier output and further connected to said reference input.

Preferably, said amplifier is an operational amplifier, wherein said first sensor is connected between a noninverting input and a reference voltage source, and wherein said second sensor is inserted in the feedback line of said amplifier, being connected between said output and an inverting input of said amplifier.

Preferably, the curves representing the resistance change of said first sensor and of said second sensor as a function of the physical quantity to be detected, have the same progression; particularly, their first and second derivatives are of the same sign.

In a preferred embodiment, said particular physical quantity is the relative humidity present in the environment where said sensors are arranged.

In a preferred embodiment, said detection means further comprise a resistance connected in parallel to said first sensor, in order to limit the resistance applied to said first input, when said first sensor has a very high resistance at low humidity values. Moreover, said detection means include, conveniently, a second resistance connected in series to said second sensor, and a third resistance connected in parallel to both said second sensor and said second resistance, in order to limit the minimum and maximum gain of said amplifier, respectively, when said second sensor is plunged in an environment with very high or very low humidity, respectively.

Preferably, said first sensor is connected between a driving signal generator and said reference voltage generator. Said driving signals are preferably comprised of a direct voltage, referred to said reference voltage, and they actuate said first sensor in order to generate said response signal, variable with humidity changes.

Preferably, said driving signals are comprised of at least two homopolar rectangular waves, having a predetermined duration; alternatively, said driving signals are comprised of at least two rectangular waves, of opposed polarity, and having a null average value, coinciding with said reference voltage.

In a preferred embodiment, each of said sensors comprises a double array of electric conductors separated from one another, deposited over an insulating support and respectively connected to said pair of electric terminals, said electric conductors being covered with a layer of a material sensitive to one of said particular physical quantities, particularly humidity, and with a permeable layer, laid upon said sensitive layer.

In a second aspect, the present invention refers to a method for detecting physical quantities which provides the following steps:
  a) driving a first sensor of a physical quantity with a predetermined driving signal in order to obtain a first output signal, function of the physical quantity;
  b) amplifying the first output signal and obtaining an amplified signal $V_o$ in response to said first output signal;
  c) driving a second sensor, arranged in the same environment as the first sensor, with a driving signal comprised of the amplified signal and obtaining a second output signal;
  d) continuously adjusting the amplification gain of the first signal as an inverse function of the value of said second output signal.

Preferably, said amplification step is carried out in a variable gain amplifier, having a noninverting input, and step b) includes applying said first output signal (V+) to said noninverting input, and step d) includes applying said second output signal (V−) to said inverting input.

In a particular embodiment of the present invention, the method for detecting physical quantities further includes converting said output signal into digital form and sending it to an electronic processor to perform a linearity correction as a function of temperature changes of said sensors based on predetermined data.

This and other features of the invention will be manifest from the following description of a preferred embodiment, made by way of a not limiting example, with reference to the attached drawings.

DETAILED DESCRIPTION OF A PREFERRED EMBODIMENT

The following description relates to a preferred embodiment of a physical quantity, particularly humidity detection device, formed of a sensor and a sensing circuit.

Although the device described in the following example is relative to a humidity sensor, the sensing circuit is suitable to detect any type of physical quantity converted into electric signals by a suitable sensor; particularly, besides humidity, the circuit object of the present invention is suitable to detect other physical quantities, such as temperature, pressure, particular characteristics of chemical compounds, gas presence, etc., using only an appropriate sensor, sensitive to a specific physical quantity to be detected.

Figure 1:
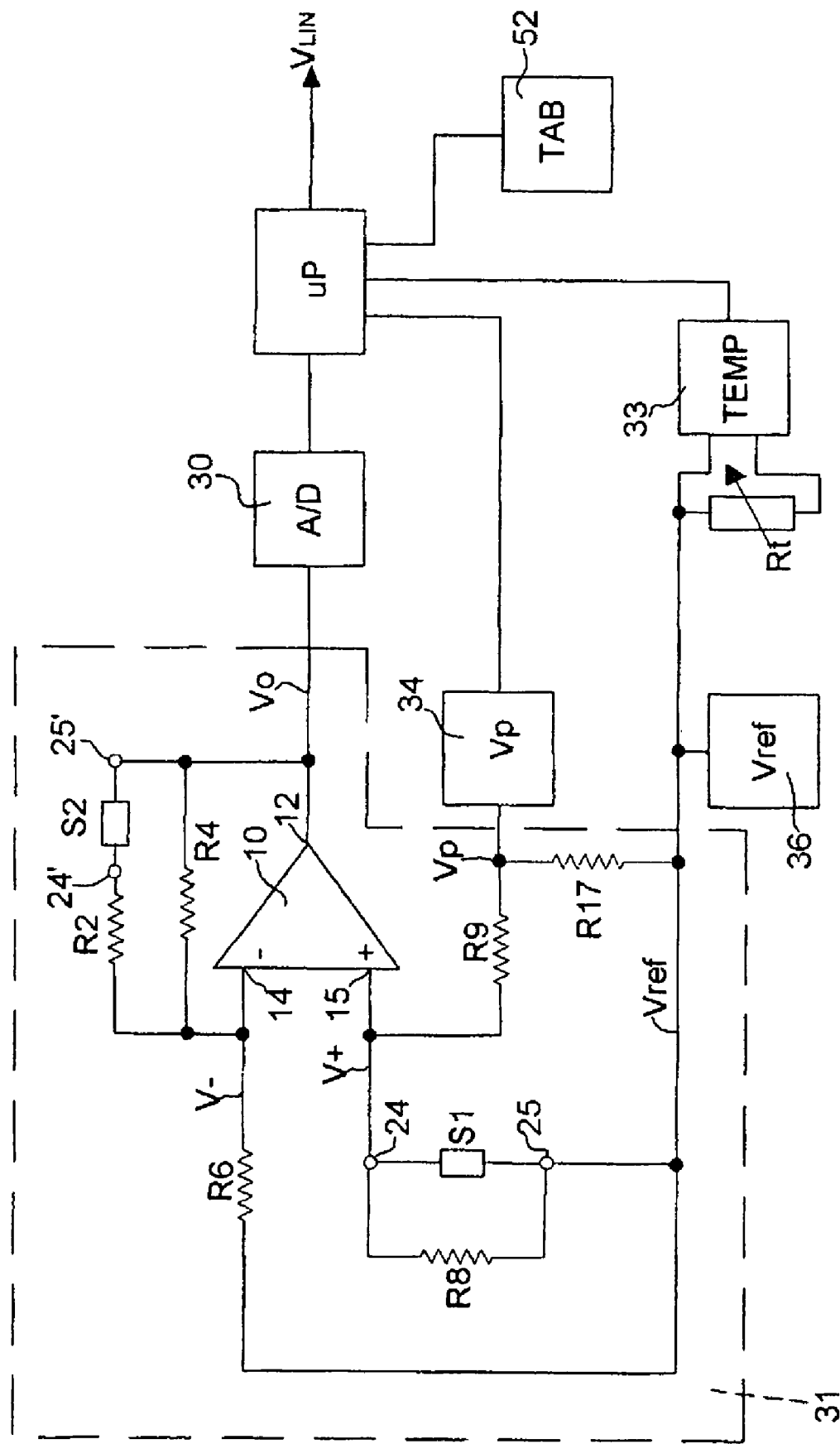
FIG. 1 depicts a functional block diagram of the humidity detection device, according to the present invention.

Referring to FIG. 1, an operational amplifier 10 having an output 12 and two inputs, respectively an inverting one 14 and a noninverting one 15, is connected to two sensors S1 and S2, arranged together in the same environment where humidity is to be detected.

Preferably, the curves representing the resistance change of the two sensors S1 and S2 as a function of humidity have the same progression; particularly their first and second derivatives are of the same sign.

More preferably, the two sensors S1 and S2 are equal, i.e. both have the same electric and, possibly, also mechanical characteristics.

Figure 2:
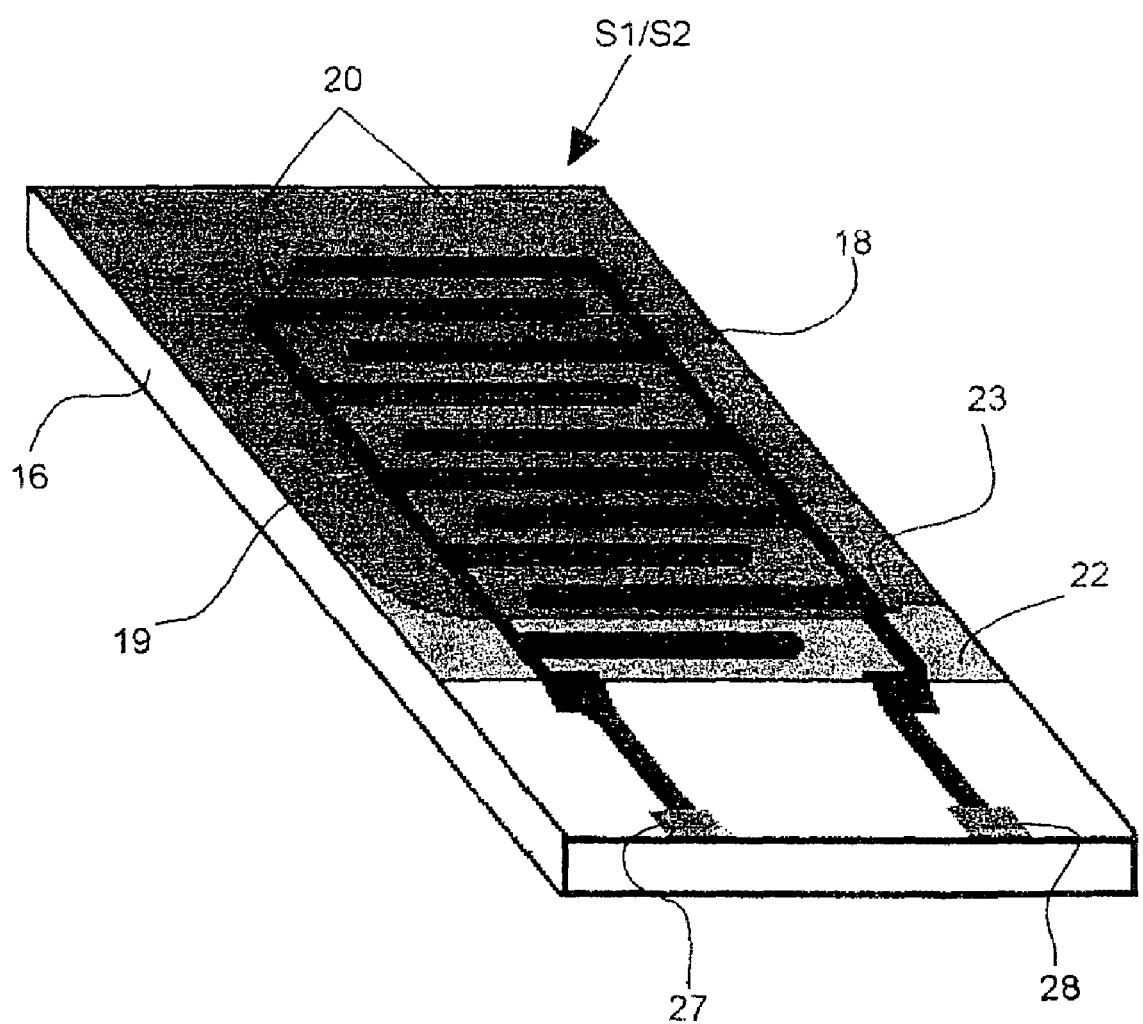
FIG. 2 depicts a humidity sensor used with the circuit of FIG. 1.

In FIG. 2 one of the two sensors S1 and S2 is shown, the structure thereof will be later described in detail.

Sensor S1 is connected with a terminal 24 to the noninverting input 15 and with another terminal 25 to a reference voltage Vref; sensor S2 is used as a feedback element of the amplifier 10, in order to modify the gain of the amplifier itself, as it will be later explained; sensor S2 is thus inserted in the feedback path of the amplifier 10 and it is more exactly connected with a terminal 24' to the inverting input 14 and with a terminal 25' to the output 12 of the amplifier 10.

Sensors of a resistive type normally show a resistance changing as a function of humidity according to a strongly non-linear law and with a very wide range of values, covering many decades, for instance five to eight decades. Effectively, resistance change is very great at low humidity values, while it approaches in an asymptotic way to zero Ohm at humidity values near to 100%. Such non-linear variation law substantially approximates a curve of a logarithmic type (FIG. 3): at low humidity values, the sensor resistance has values of several MOhm, for example 5–20 MOhm (portion A); it falls quickly to values of some tens of kOhm in the region of greater curvature (portion B), with a humidity of 15–40%, and it reaches in an asymptotic way very low resistance values (portion C) in the order of some kOhm, or even less, for humidity values comprised between about 40% and 100%.

Sensor S1 is connected in parallel to a resistance R8 connected between terminals 24 and 25 of sensor S1, which value is chosen substantially equal to the resistance value of sensor S1 as measured at an intermediate humidity, e.g. RH=40–50%.

Second sensor S2 is connected in series with a resistance R2 of a value, for instance, of some kOhm. In parallel to group S2, R2, a resistance R4 is connected, of a value much higher than R2, for instance of some MOhm.

Any differences of the resistance value of one sensor compared to the other can be compensated, at least partially, by properly choosing the values of resistances R2, R4 and R8.

Voltage response V+ of sensor S1 applied to the noninverting terminal 15 of the amplifier 10 is referred to a reference voltage Vref, as indicated in FIG. 1, wherein, for example, a value of 2.5 Volts is assigned to the reference voltage Vref; voltage Vref is suitable to provide to the operational amplifier 10, an operating voltage level, intermediate between power supply and ground, to which the response signal V+ of the sensor S1 and the driving voltages Vp are referred; the reference voltage is supplied by an auxiliary circuit 36, connected to the terminal 25 of sensor S1 and to the inverting input 14 of the amplifier 10, through resistance R6.

The analogue signal $V_o$ at the output of amplifier 10 can be processed through processing known by those skilled in the art.

The sensor S2 being inserted in the feedback branch of amplifier 10, and its resistance changes being proportional to those of sensor S1, the amplifier 10 gain is modified with a progression congruent with the progression of the signal generated by sensor S1, but in an inverse way, producing, as a resulting signal at the output of amplifier 10, a voltage $V_o$ (FIG. 4), having a substantially linear progression, as the humidity value changes.

Referring to FIG. 1, the resistance R8, in parallel to sensor S1, intervenes to limit the voltage applied to the noninverting input 15, when sensor S1 shows very high voltage at low humidity values; while, at high humidity values, when sensor S1 shows low resistance values, i.e. lower than resistance R8, the latter affects S1 in a negligible way.

Resistances R2 and R4 act in a similar way; resistance R4 has a very high resistive value, as already mentioned, approximately of the same order of magnitude as the resistance values of sensor S2 at low humidity; therefore resistances R2 and R4 intervene to limit the minimum and the maximum gain of the amplifier 10, respectively, when sensor S2 is plunged in an environment with very high or very low humidity, respectively.

In case it is desired to increase the linearity degree of the response, the output 12 of the amplifier 10 is conveniently connected to an Analogue-to-Digital converter 30, of a type known in the art, which is in turn connected to a microprocessor uP; the converter 30 converts the analogue signal $V_o$ provided by the amplifier 10 and representative of the relative humidity value (RH) measured by sensor S1, into a digital signal suitable to be processed by microprocessor uP.

The microprocessor uP processes humidity values received from converter 30 by means of a predetermined algorithm and based on corrective parameters stored in an electronic table 52, to perform a more exact linearization of the analogue signal $V_o$.

The content of table 52 is previously calculated by microprocessor uP, in an initial calibration step, or it is provided thereto based on previously detected data.

In case it is desirable to increase the linearity degree of the response, eliminating or reducing the thermal drifts effects, data provided by a temperature compensation circuit 33 must be taken into account; the circuit 33, of a known type, detects and amplifies the signals generated by a resistance Rt, variable with sensor S1 temperature.

The processing of the signal $V_o$ by microprocessor uP actually consists of a double form of compensation; a first compensation is made to correct any deviation from linearity, using table parameters obtained from the preliminary calibration, and a second temperature compensation using the response of the thermal compensation circuit 33.

Preferably, the two compensations are made simultaneously.

Figure 5:
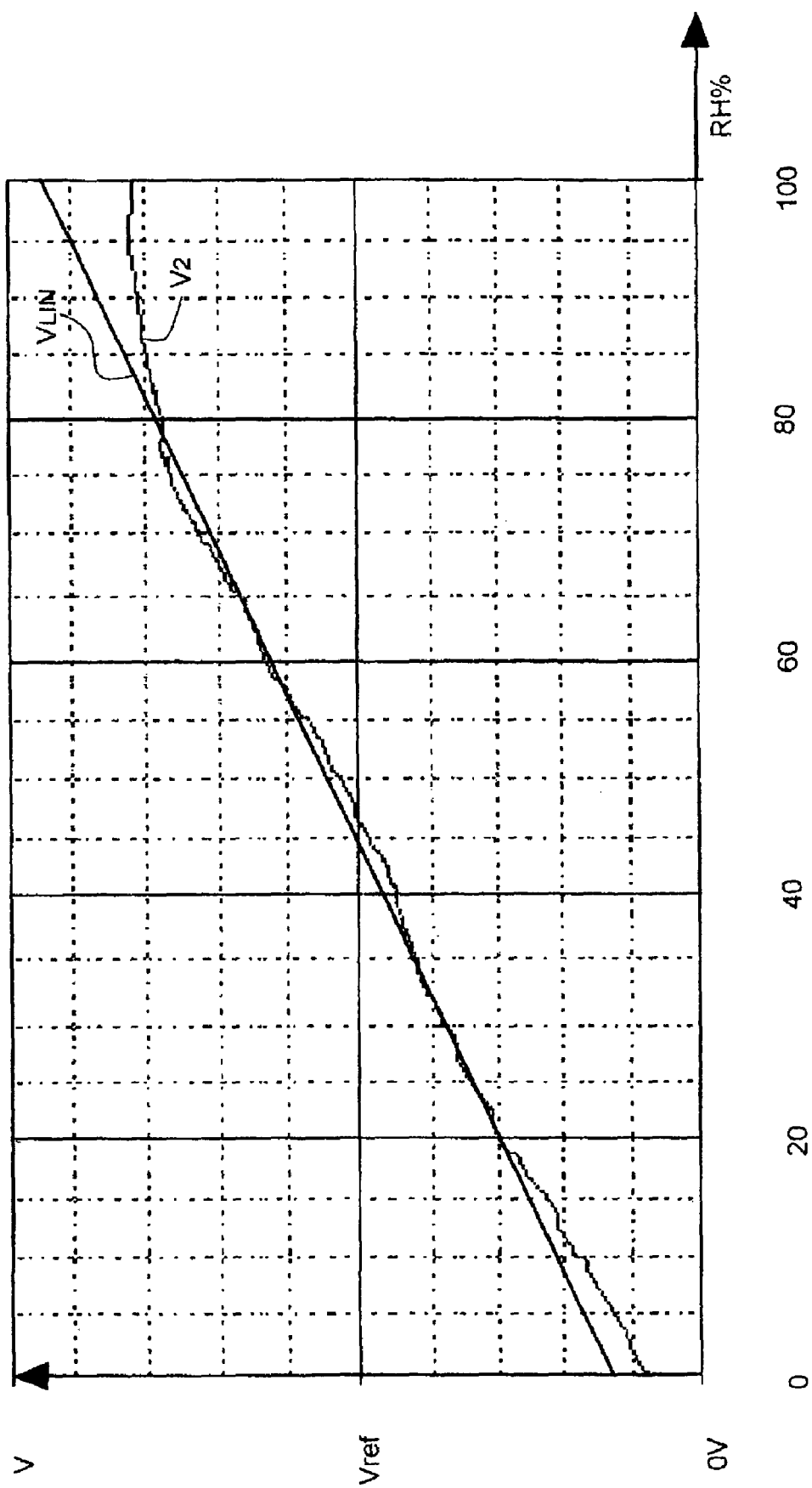
FIG. 5 depicts the progression of the humidity representing signal as applied to the A/D converter and, linearized, after the processing by the uP microprocessor.

At the end of the processing, the signal representing humidity values, variable according to a linear law, transformed by microprocessor uP, is represented by diagram $V_{LIN}$ in FIG. 5.

As shown in FIG. 1, sensor S1 is driven by a voltage signal Vp, later referred to as the driving signal, generated by a circuit 34, which receives from microprocessor uP the activation signals suitable to drive sensor S1 in the most appropriate way in order to obtain, as a response, a measurement of humidity as a function of the electro-physical characteristics of the sensitive material used.

Figure 6:
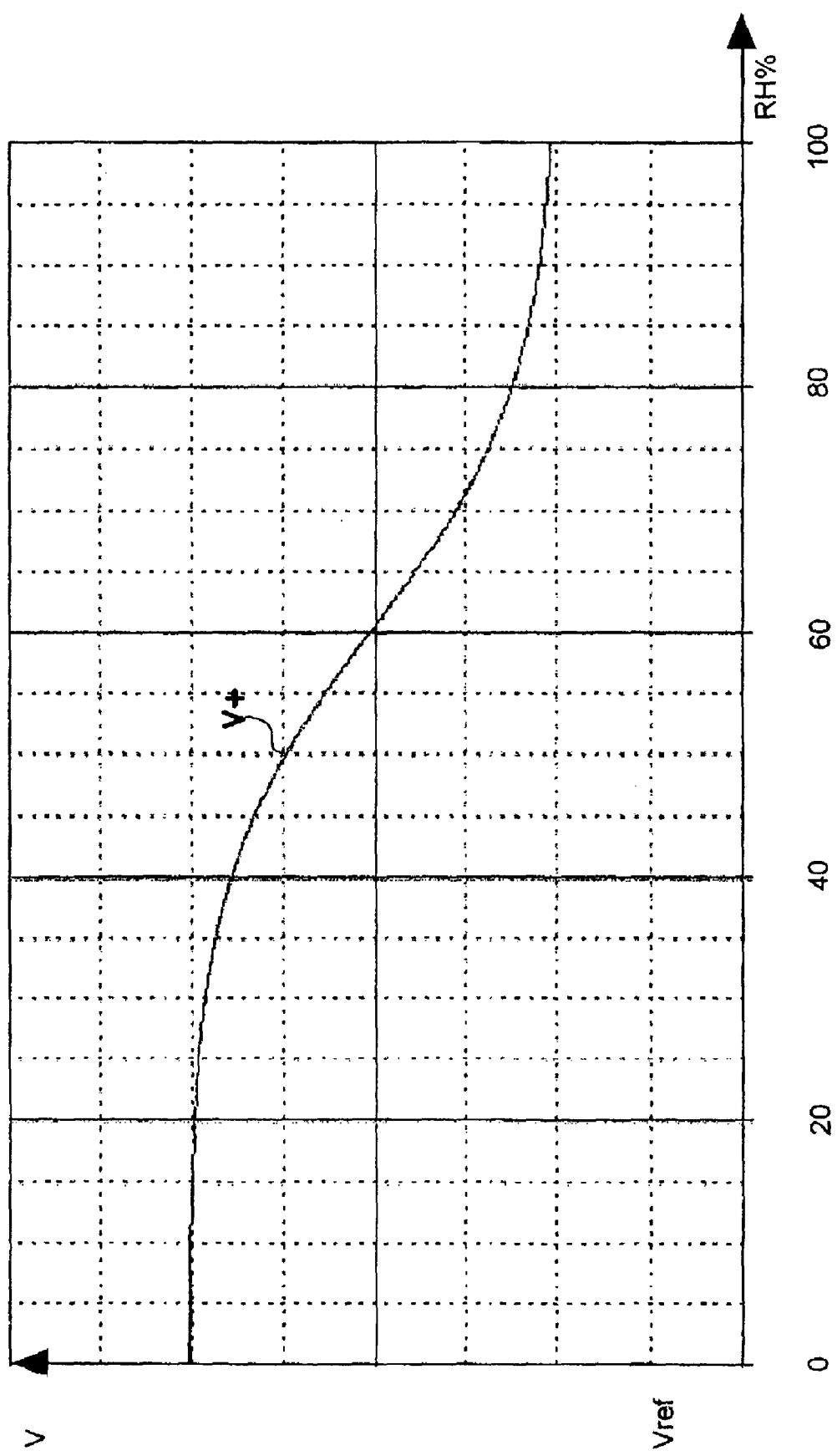
FIG. 6 depicts the progression of the humidity representing signal at the noninverting input of the amplifier 10.

In FIG. 6 the progression of the voltage signal V+ at the sensor S1 output is represented; from this signal the impossibility is manifest of exactly reading on the curve the change of voltage V+ as humidity changes, in the case a voltage is applied to only one sensor, without making use of the invention device.

Description of the Sensor

The two sensors S1 and S2, similar to each other, are conveniently made with the same sensitive material, and the same construction specifics, electric (and possibly mechanical) characteristics, so that they have a resistance progression as a function of humidity as similar as possible; particularly, it is appropriate that the curves representing the resistance change of the two sensors S1 and S2 as a function of humidity have first and second derivatives of the same sign (at least in the foreseen measurement range).

In such a manner, it is obtained that an analogous behaviour occurs for both sensors in the resistance change with humidity (or other quantity) changes. For instance, this means that if, for one sensor, in a first humidity range the resistance changes within a few Ohm, while in a second humidity range of a similar width the resistance changes by many tens of Ohm, for the other sensor it is necessary that the resistance increases by passing from the first to the second range and also that the resistance increase changes in the same way.

The better the linearization of the signal representing humidity values $V_{LIN}$ that is obtained, the less the difference between the resistances of the two sensors, at a given humidity value.

The sensors S1 and S2 are comprised of a ceramic, porous support 16 (FIG. 2), e.g. of alumina, on which two arrays 18 and 19 of conductive electrodes 20 are placed, deposited with any one of the known electrodeposition processes with the aid of a mask; the electrodes of the two arrays 18 and 19 are arranged in an interdigited form, i.e. alternately interposed between and insulated from one another.

The conductors 20 of each array 18 and 19 respectively lead to the two connection terminals 27 and 28, for the connection of the two sensors S1 and S2 to the operational amplifier 10 (FIG. 1).

A first layer 22 of a material sensitive to humidity is placed over the two arrays 18 and 19 of electrodes 20, and it is in turn covered by a second layer 23 of insulating, protective and permeable to water material.

The first layer 22 sensitive to humidity is comprised of one of the compounds known in the art, for example the compounds chosen among conductive hydrophilic polymers, sintered ceramic powders, resins, or properly treated metal salt-based compounds.

According to a preferred embodiment of the humidity detection device, according to the present invention, the first layer 22 sensitive to humidity of each of the two sensors S1 and S2 can be preferably comprised of a resistive type material, which has superior reproducibility and reliability characteristics and lower manufacturing costs with respect to other types of materials. For instance the sensor can have a size of 12 mm×5 mm×0.5 mm and for the layer 22 a polyelectrolyte can be used, as for example sodium sulphate polystyrene (NaPSS).

A sensor of this kind is described in the Chinese patent CN 2543063Y.

The second protective layer 23 is preferably comprised of a material permeable to water, as for example, a celluloid layer.

Description of an Alternative Form of the Sensing Circuit

Figure 7:
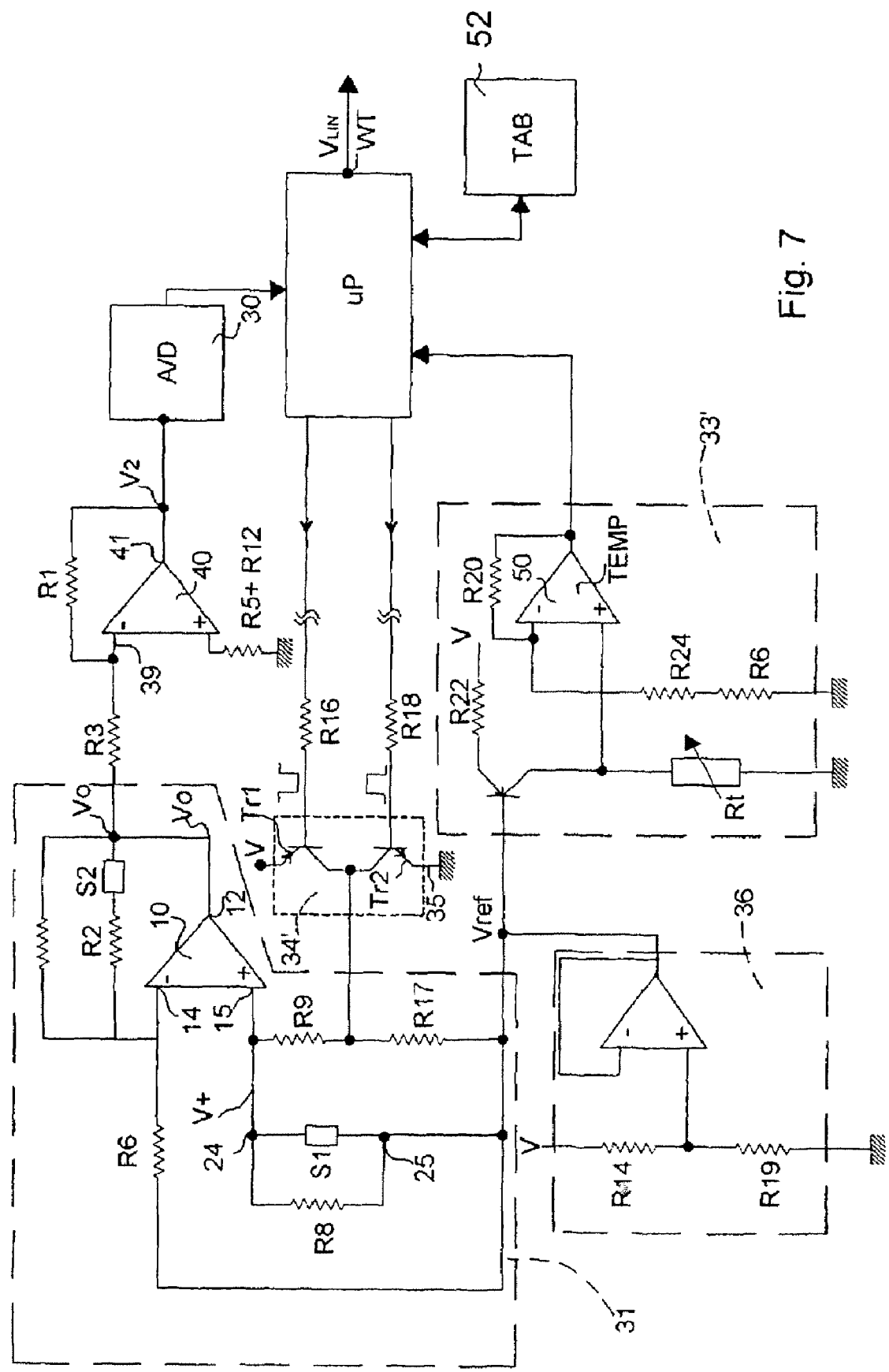
FIG. 7 depicts a different embodiment of the sensing circuit of FIG. 1.

Referring to FIG. 7, a different embodiment of a humidity sensing circuit according to the invention is described by way of a not limiting example, that is suitable to be associated to two sensors which use a humidity sensitive material comprised of a ionic conduction polymeric electrolyte, of the type of the one described in the U.S. Pat. No. 4,642,601.

Therefore in FIG. 7 the portion regarding the amplifier 10 and the related passive components, enclosed in a dashed rectangle 31, and that for simplicity are called detection means, does not change and its description will not be repeated here.

Using, as humidity sensitive material, a ionic conduction material, humidity detection is based on a characteristic property of such material, i.e. on the phenomenon according to which the ionic dissociation degree changes, according to whether the humidity level increases or decreases; on the ionic concentration in the material depend the electric characteristics of the material itself, and particularly the capability of separating positive from negatives ions, upon application of a potential difference; in other words, as the humidity level changes, the ionic dissociation degree correspondingly changes, causing a related change of the electric impedance of the sensitive material.

Figure 3:
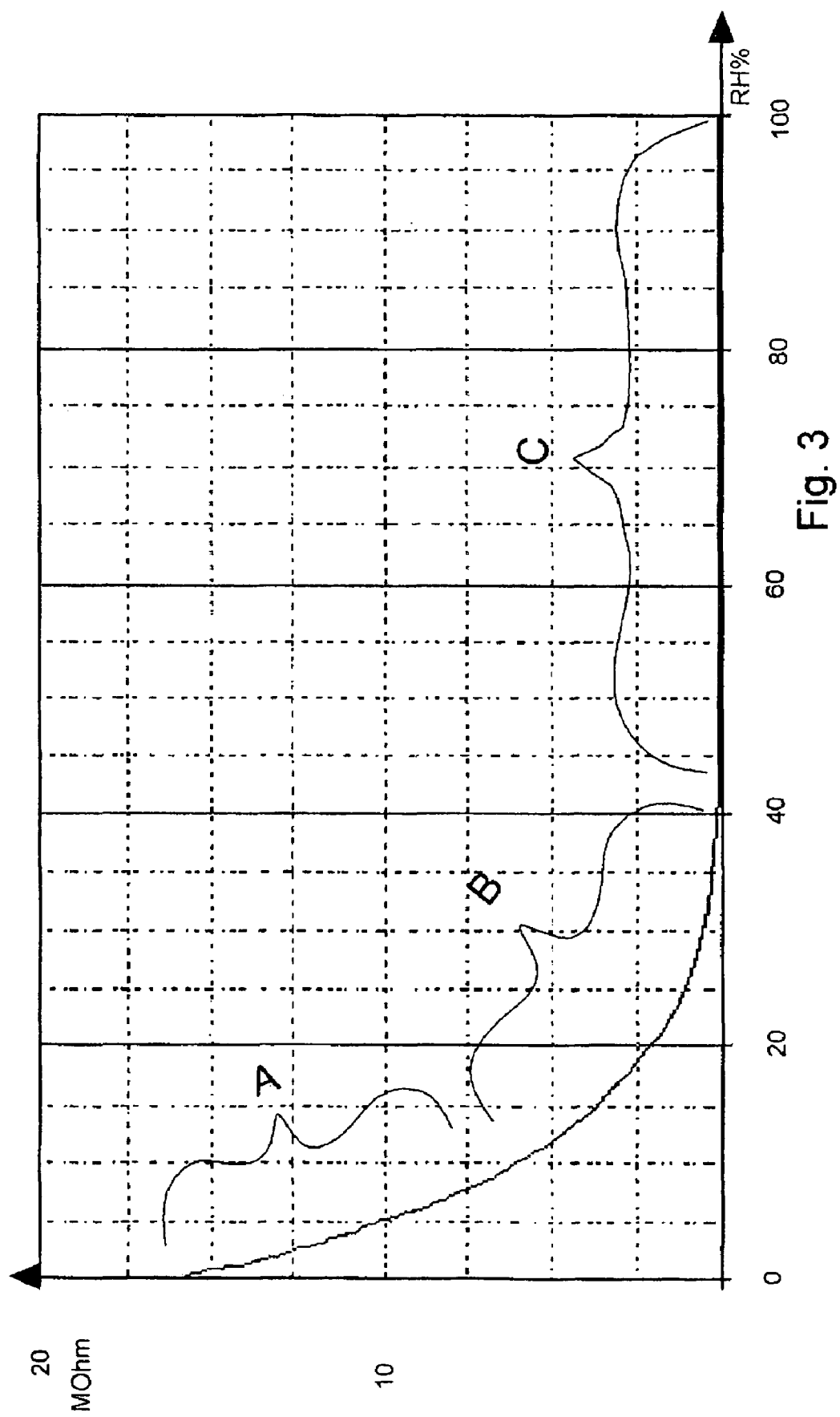
FIG. 3 depicts the typically logarithmic variation law of the resistance as a function of the humidity of the sensor of FIG. 2.

In the specific case, the sensors S1 and S2 have an electric impedance, as seen from connection terminals 27 and 28, created by a resistance Rs in parallel to a capacity Cs, wherein its value is normally very little, so that due to the resistance Rs effect prevailing over the capacity Cs, the impedance change as humidity changes takes up a progression similar to that of a sensor of the resistive type, i.e. according to a substantially logarithmic law (FIG. 3).

Because the electric response of the ionic conduction polymeric material that comprises the sensitive layer of the sensors S1 and S2 is determined, as seen above, by the transportation of ions and the capacitance between electrodes connected to it, to measure the polyelectrolyte impedance as a function of environmental humidity, the sensor S1 is driven with a driving signal comprised of an alternating voltage Vp; such alternating voltage is preferably comprised of two successive square waves.

The driving signals are generated by a circuit 34' (FIG. 7), comprised of a pair of transistors Tr1 and Tr2 of opposed polarity and connected in series between the supply voltage V and the ground 35; transistors Tr1 and Tr2 bases are alternately driven by microprocessor uP, which, in a way known to those skilled in the art, is programmed to send activation pulses for one or the other of the transistors Tr1, Tr2, properly clocked.

The analogue signal $V_o$, representative of the humidity value at the output 12 of the amplifier 10, is sent through a resistance R3 to the inverting input 39 of a second operational amplifier 40, to adapt the level of signal $V_o$ to the characteristics of a converter 30, for a subsequent conversion of the signal $V_o$ into digital form. At the output 41 of the amplifier 40 there is thus a signal $V_2$ corresponding to the signal $V_o$, but overturned, as indicated in FIG. 5.

The sensing circuit of FIG. 7 also includes a circuit 33', similar to circuit 33 of FIG. 1, for compensating the temperature of sensors S1 and S2, wherein an operational amplifier 50 amplifies a signal generated by a thermistor $R_t$, which detects temperature changes in the proximity of sensors S1 and S2, and sends such amplified signal to microprocessor uP, which, by means of an algorithm, calculates corrective coefficients which are preliminarily stored in the table 52, contained in an internal memory of the same microprocessor.

Figure 4:
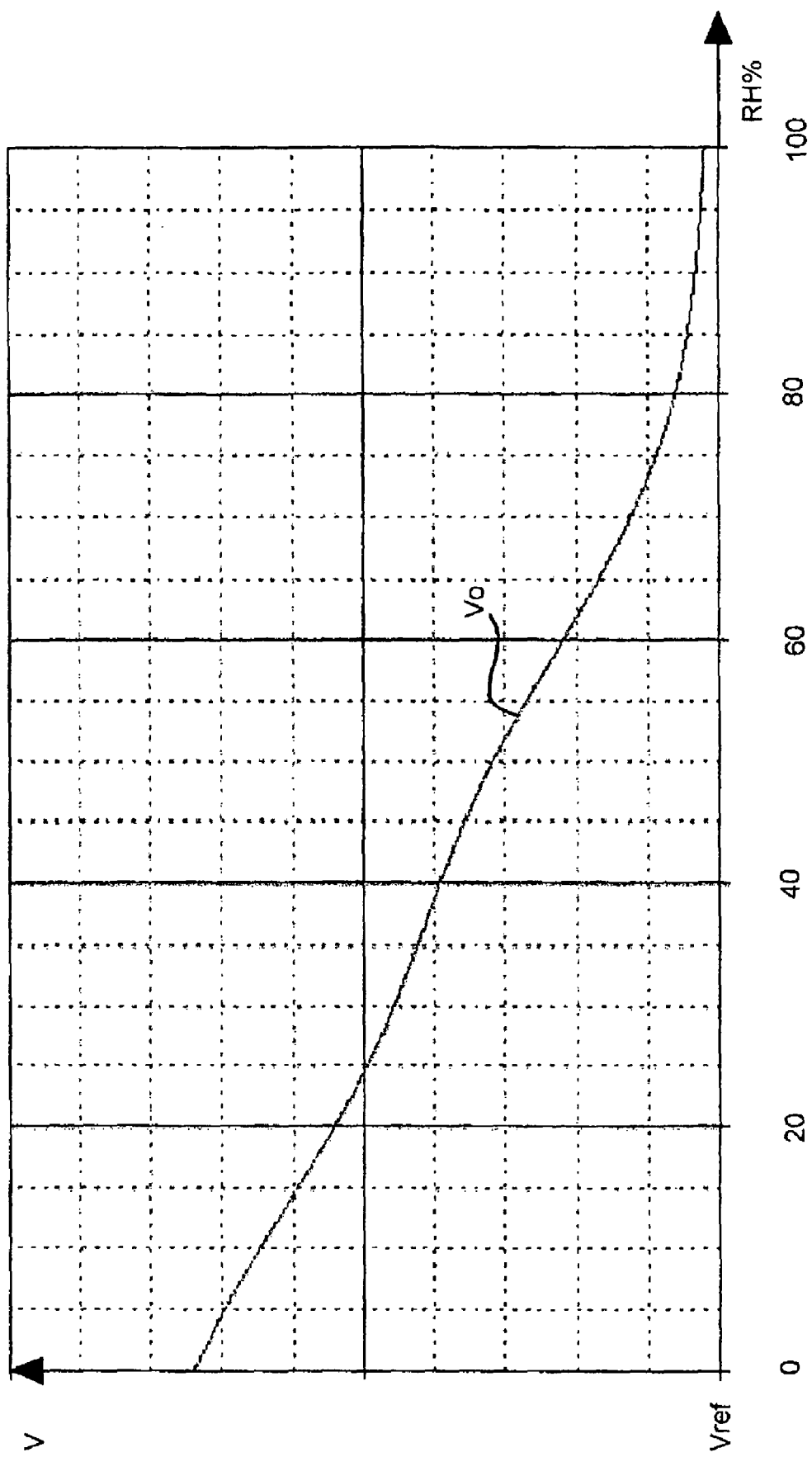
FIG. 4 depicts the progression of the humidity representing signal at the amplifier output 10.

Signals $V_o$ and $V_{LIN}$ respectively present at output 12 of the amplifier 10 and at output OUT of the microprocessor uP relating to the circuit of FIG. 7, are represented in FIGS. 4 and 5.

It is understood that modifications and/or replacements of components can be made to the humidity detection device, according to the present invention, without however departing from the scope of the invention.

For example, the operational amplifier 10 can be replaced by an amplifier circuit made with discrete components, as junction transistors, or field effect transistors, and with their relative resistive and capacitive polarization and compensation components, respectively.

Similarly, sensors S1 and S2 can be made with different materials from those indicated in the description of the sensor of FIG. 2; for example, the support 16 can be made with a semiconductor silicon chip, passivated with a layer of silicon oxide and protected by a layer of silicon carbide and nitride, superposed to the silicon oxide layer.

The electrodes 20 are deposited through any of the well-known methods of thin film deposition with the aid of masks. Preferably, the electrodes 20 are obtained by evaporation or sputtering.

Both the sensors S1 and S2 and the detection circuit 31 can be manufactured with the known miniaturizing techniques and enclosed in a metallic capsule, provided with suitable openings for the passage of humidity of the environment where the capsule is placed. The other circuit components illustrated in FIG. 7, being bigger, are normally placed in a remote position relative to the capsule, and connected to it through cables.

The invention claimed is:

1. A physical quantity detection device, including a sensor, sensitive to said physical quantity and exposed thereto, and an amplifier, connected to the output of said sensor with a first input and having a second reference input, characterized in that it comprises a second sensor, sensitive to said physical quantity and exposed thereto, connected to the amplifier output and connected also to said reference input.

2. A detection device, according to claim 1, characterized in that said amplifier is an operational amplifier, wherein said first sensor is connected between a noninverting input and a source of a reference voltage, and wherein said second sensor is arranged in the feedback line of said amplifier, being connected between said output and an inverting input of said amplifier.

3. A detection device, according to claim 1, characterized in that said first and second sensors are made with the same sensitive material.

4. A detection device, according to claim 3, characterized in that the curves representing the resistance change of said first sensor and of said second sensor as a function of the physical quantity to be detected have the same sign of the first derivative and second derivative.

5. A detection device, according to claim 4, characterized in that said particular physical quantity is the relative humidity present in the environment where said sensors are arranged.

6. A detection device, according to claim 2, characterized in that it further comprises a resistance connected in parallel to said first sensor, to limit the resistance applied to said first input, when said first sensor has a very high resistance at low humidity values.

7. A detection device, according to claim 2, characterized in that it comprises a second resistance connected in series to said second sensor and a third resistance connected in parallel to both said second sensor and said second resistance, to limit the minimum and maximum gain of said amplifier, respectively, when said second sensor is plunged in an environment with very high or very low humidity, respectively.

8. A detection device, according to claim 6, characterized in that said first sensor is connected between a generator of driving signals and said reference voltage generator, said driving signals activating said first sensor to generate said response signal, variable as humidity changes.

9. A detection device, according to claim 8, characterized in that said driving signals are comprised of a direct voltage, referred to said reference voltage.

10. A detection device, according to claim 8, characterized in that said driving signals are comprised of at least two homopolar square waves, having a predetermined duration.

11. A detection device, according to claim 8, characterized in that said driving signals are comprised of at least two square waves of opposed polarity, and having a null average value, coinciding with said reference voltage.

12. A detection device, according to claim 10, characterized in that said at least two square waves have the same amplitude.

13. A detection device, according to claim 9, characterized in that said driving signals are referred to said reference voltage.

14. A detection device, according to one of the preceding claims, characterized in that each of said sensors includes a double array of electric conductors separated from one another, deposited on an insulating support and respectively connected to said pair of electric terminals, said electric conductors being covered with a layer of a material sensitive to one of said particular physical quantities, and with a permeable layer laid upon said sensitive layer.

15. A detection device, according to claim 14, characterized in that said particular physical quantity is the relative humidity present in the environment where said sensors are arranged.

16. Method for detecting physical quantities, providing the following steps:
   a) driving a first sensor of a physical quantity with a predetermined driving signal in order to obtain a first output signal, function of the physical quantity;
   b) amplifying the first output signal and obtaining an amplified signal in response to said first output signal;
   c) driving a second sensor, arranged in the same environment as the first sensor, with a driving signal comprised of the amplified signal and obtaining a second output signal;
   d) continuously adjusting the amplification gain of said first signal as an inverse function of the value of said second output signal.

17. A method for detecting physical quantities according to claim 16, characterized in that the curves representing the resistance change of said first sensor and of said second sensor as a function of the physical quantity to be detected have the same sign of first derivative and second derivative.

18. A method for detecting physical quantities according to claim 16, characterized in that the said amplification step is carried out in a variable gain amplifier, having a noninverting input, and step b) includes applying said first output signal to said noninverting input.

19. A method for detecting physical quantities according to claim 16, characterized in that said amplification step is carried out in a variable gain amplifier, having an inverting input, and step d) includes:
   applying said second output signal to said inverting input.

20. A method for detecting, according to claim 16, further comprising:
   e) converting said output signal into digital form and sending it to an electronic processor to carry out a linearity correction as a function of the temperature changes of said sensors based on predetermined data.

* * * * *